(12) United States Patent
Hargreaves et al.

(10) Patent No.: US 9,921,107 B2
(45) Date of Patent: Mar. 20, 2018

(54) ADAPTATION OF FIELD USE SPECTROSCOPY EQUIPMENT

(71) Applicant: Thermo Scientific Portable Analytical Instruments Inc., Tewksbury, MA (US)

(72) Inventors: Michael Derek Hargreaves, Burlington, MA (US); Timothy M. Pastore, Wakefield, MS (US); Gregory H. Vander Rhodes, Melrose, MA (US); Brendon D. Tower, Weymouth, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 0 days.

(21) Appl. No.: 15/363,186

(22) Filed: Nov. 29, 2016

(65) Prior Publication Data

US 2017/0314992 A1    Nov. 2, 2017

Related U.S. Application Data

(63) Continuation of application No. 14/579,832, filed on Dec. 22, 2014, now Pat. No. 9,513,167.
(Continued)

(51) Int. Cl.
*G01N 21/00*     (2006.01)
*G01J 3/44*      (2006.01)
(Continued)

(52) U.S. Cl.
CPC ........... *G01J 3/4412* (2013.01); *G01J 3/0264* (2013.01); *G01J 3/0272* (2013.01); *G01J 3/0283* (2013.01);
(Continued)

(58) Field of Classification Search
CPC ........ G01J 3/44; G01J 3/02; G01J 3/51; G01J 3/513; G01N 21/65; G01N 15/1459
See application file for complete search history.

(56) References Cited

U.S. PATENT DOCUMENTS 5,841,139 A    11/1998  Sostek et al.
7,057,721 B2    6/2006  Gardner, Jr. et al.
(Continued)

FOREIGN PATENT DOCUMENTS

WO    2008100582 A2    8/2008
WO    2005060380 A2    7/2015

*Primary Examiner* — Abdullahi Nur
(74) *Attorney, Agent, or Firm* — William R. McCarthy, III

(57) ABSTRACT

A spectrometer system comprising a housing configured as a handheld device with a screen; a source of narrow band illumination; a sensor that detects Raman scattering signals; a source of wide band illumination; an optical element that detect Fourier transform infrared (FTIR) signals; a memory device comprising a library of information with Raman scattering reference information and FTIR reference information; and a processor configured to execute software instructions, wherein the software instructions are configured to: direct the narrow band illumination to the sample; detect the Raman scattering signals; direct the wide band illumination to the sample; detect the FTIR signals; determine a composition of the sample from a similarity between the Raman scattering spectral information and the Raman scattering reference information, and from a similarity between the FTIR spectral information and the FTIR reference information; and display the composition of the sample on the screen.

22 Claims, 9 Drawing Sheets

Related U.S. Application Data

(60) Provisional application No. 61/920,230, filed on Dec. 23, 2013.

(51) Int. Cl.
*G01J 3/02* (2006.01)
*G01N 21/65* (2006.01)
*G01N 21/35* (2014.01)
*G01J 3/453* (2006.01)
*G01J 3/45* (2006.01)
*G01J 3/28* (2006.01)

(52) U.S. Cl.
CPC ........... *G01J 3/0286* (2013.01); *G01J 3/0291* (2013.01); *G01J 3/28* (2013.01); *G01J 3/44* (2013.01); *G01J 3/45* (2013.01); *G01J 3/453* (2013.01); *G01N 21/35* (2013.01); *G01N 21/65* (2013.01); *G01J 2003/2833* (2013.01); *G01N 2021/3595* (2013.01); *G01N 2201/0221* (2013.01)

(56) References Cited

U.S. PATENT DOCUMENTS

| | | | |
|---|---|---|---|
| 7,072,770 B1 | 7/2006 | Schweitzer et al. | |
| 7,254,501 B1 | 8/2007 | Brown et al. | |
| 7,928,391 B2 | 4/2011 | Azimi et al. | |
| 2009/0237647 A1* | 9/2009 | Azimi | G01J 3/02 356/51 |
| 2010/0315629 A1 | 12/2010 | Knopp et al. | |
| 2014/0005980 A1 | 1/2014 | Green et al. | |

* cited by examiner

Fig. 3

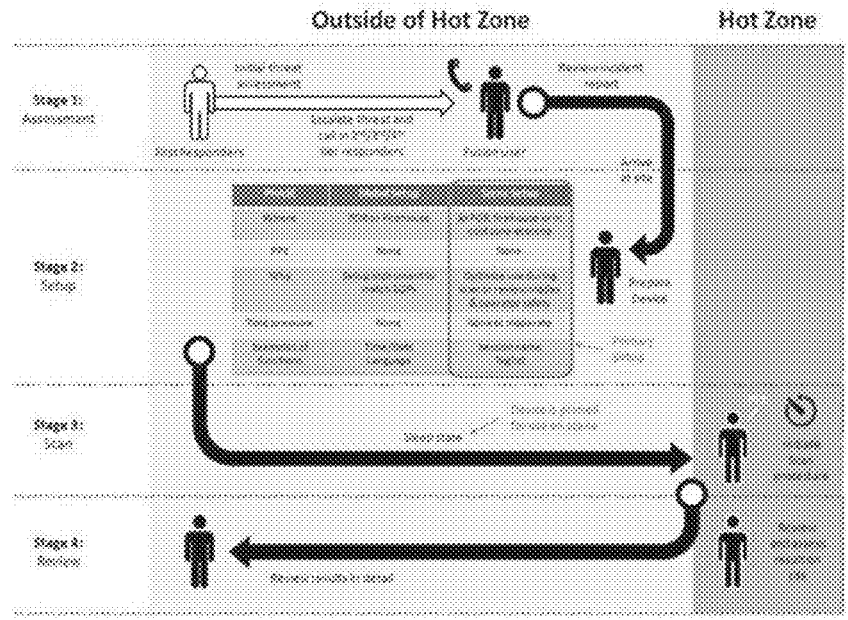

Fig. 4

| PHASE | Global Setup | Scene Setup | Scan | Review/Response |
|---|---|---|---|---|
| Where | FOB or Firehouse | At FOB, firehouse or in cold zone at scene | In hot zone | In hot zone or in cold zone |
| PPE | None | None | None to Level A | None to Level A |
| Why | Setup instrument to match SOPs | Optimize use during scan or review modes & operator safety | What is it? Am I adequately protected? | What do I do now? Need more info to respond |
| Time pressure | None | Moderate | High | Moderate to high |
| Examples of functions | Time/Date Language | Session name Tag list | FTIR, Raman, Wizard | Spectrum Export scan |

ADAPTATION OF FIELD USE SPECTROSCOPY EQUIPMENT

CLAIM OF PRIORITY

This application is a continuation of and claims priority to U.S. patent application Ser. No. 14/579,832 filed Dec. 22, 2014, which claims priority to U.S. provisional patent application No. 61/920,230, filed Dec. 23, 2013. The contents of each application is hereby incorporated by reference herein in its entirety for all purposes.

GOVERNMENT SUPPORT

This invention was made with Government support under Contract Number N00174-13-C-0032 awarded by Naval Explosive Ordnance Disposal Technology Division (NAVEODTECHDIV). The Government has certain rights in the invention.

BACKGROUND

Field of the Invention

The invention relates to field use spectroscopy equipment, and in particular, to adaptation of radiological and/or optical detection and/or identification equipment.

Description of the Related Art

A variety of instruments are used in the field to assist with hazard assessment and control. When users, whether it be a first responder or soldier, are called to respond to a situation, they frequently have some intelligence about the situation. In the case of a first responder, they have information from a call to emergency services where somebody may have explained what happened. In the case of a soldier, the infantry scouting a territory will identify something suspect and call in the appropriate personnel. When these users arrive on scene they frequently are under time constraints to prepare their tools and respond. In the case of the soldier, they may be getting shot at. In the case of the first responder, there may be victims that need rescuing or pressure to reopen an evacuated building. Making proper assessments with such instruments is only complicated by the increasing complexity of these tools. Accordingly, whether the responder is under a time constraint, or is not adequately familiar with the instrument, setting the various parameters can be a challenge.

Some of these instruments allow for configuration of the instrument to optimize performance. This optimization may be to have the instrument detect/identify or alarm on a specific kind of chemical, or list of chemicals. The optimization may be to improve performance, user safety or to have the instrument perform in accordance with the standard operating procedures (SOP). Current instruments that allow for user configuration offer a manual process that permits editing the settings one at a time. Manual configuration takes time, while the user is under time constraints, and therefore many times the instruments are not configured for optimal performance. This puts the users at risk and slows down the response.

What are needed are methods and apparatus for adapting or reconfiguring field instruments. Preferably, the solutions make use of field intelligence to assist a user with configuration control. Additionally, the solutions should be expedient and provide for improved performance of the instrumentation.

In addition, there is an ever increasing need for field-portable analyzers capable of reliably identifying unknown materials. Emergency response teams and law enforcement agencies frequently encounter unknown and potentially hazardous substances including toxic industrial chemicals (TICs), narcotics, explosives precursors, and improvised explosive devices (IEDs). In addition to these substances, conventional explosives, biological weapons, and chemical weapons continue to be threats for homeland security and military users. In the laboratory environment, mid-infrared and Raman spectroscopy have proven very effective for identifying such materials. Efforts to transition vibrational spectroscopy from a laboratory analytical technique to a field based tool have been on-going for more than a decade, and in recent years handheld spectrometers have been widely successful in a number of applications.

Field users of handheld spectrometers typically do not have extensive training in science or spectroscopy. As such, an important design consideration for such devices is to incorporate on-board intelligence capable of converting raw spectral data into answers. In qualitative applications, the question being asked by the end user frequently falls into one of three categories:

1) authentication: Is the measured test material consistent with genuine substance X?

2) screening: Does the measured test material appear to contain substance X?

3) identification: What material was measured?

The problem associated with authentication is quite bounded (e.g., "Is the measured spectrum consistent with a stored reference spectrum of material X?"). Authentication algorithms are typically used for raw material confirmation and anti-counterfeiting applications, and will not be considered further herein.

Screening algorithms evaluate whether at least a subset of features in an unknown measurement correspond to one or more specific substances of interest. Such algorithms require user input regarding the potential presence of materials (e.g., what test targets are being searched for, and what interferents are likely to be encountered). Thus, the screening application is also bounded, albeit not to the extent that authentication is. As such, screening algorithms are most attractive for scenarios where the instrument operator has knowledge regarding the potential presence of specific analytes.

Identification, or library searching, algorithms are configured to scour a library of known materials and determine whether the unknown spectrum is consistent with any stored responses from the database. While lower-end devices stop with pure material assessment, more sophisticated identification equipment incorporates automatic mixture analysis that is invoked if the unknown measurement does not match any library spectra. The mixture analysis is performed to determine whether a combination of stored responses explaining a significant portion of the measured data can be found. This is of great practical utility as samples encountered in the field are frequently impure. Identification algorithms are very flexible in the sense that they can identify an unknown material from many thousands of possible candidates; however, they do not incorporate information regarding the potential presence of specific analytes the same way that screening algorithms do. Thus, screening algorithms often provide enhanced detection capability which makes them attractive for specific applications such as chemical warfare agent or narcotics detection.

Portable analytical devices based on a range of technologies, such as infrared spectroscopy, Raman spectroscopy, X-ray fluorescence spectroscopy, mass spectrometry, etc. are now widely available and deployed globally. However, there is a continuing need for a spectrometer that combines a sensor adapted for providing Fourier transform infrared spectroscopy (FTIR) surveillance and a sensor for providing Raman spectroscopy surveillance.

SUMMARY

An embodiment of a spectrometer system is described that comprises a housing configured as a handheld device and comprising: a screen; a source of narrow band illumination configured to illuminate a sample with light; a sensor configured to detect Raman scattering signals in response to the narrow band illumination from the sample; a source of wide band illumination configured to illuminate a sample with light; an optical element configured to detect Fourier transform infrared signals in response to the wide band illumination from the sample; a memory device comprising a library of information, wherein the library of information comprises a set of Raman scattering reference spectral information and a set of Fourier transform infrared reference spectral information; and a processor configured to execute software instructions, wherein the software instructions are configured to: direct the narrow band illumination to the sample; detect the Raman scattering signals comprising spectral information from the sample; direct the wide band illumination to the sample; detect the Fourier transform infrared signals comprising spectral information from the sample; determine a composition of the sample from a similarity between the detected Raman scattering spectral information and the set of Raman scattering reference spectral information, and from a similarity between the detected Fourier transform infrared spectral information and the set of Fourier transform infrared reference spectral information; and display the composition of the sample on the screen.

BRIEF DESCRIPTION OF THE DRAWINGS

The features and advantages of the invention are apparent from the following description taken in conjunction with the accompanying drawings in which:

FIG. 3 is an illustration of the stages for use of the instrument of FIG. 1;

FIG. 4 is a table presenting exemplary considerations for setup and use of the instrument of FIG. 1; and, FIG. 5 is a table depicting aspects of response profiles for configuring the instrument of FIG. 1.

DETAILED DESCRIPTION

Figure 1:
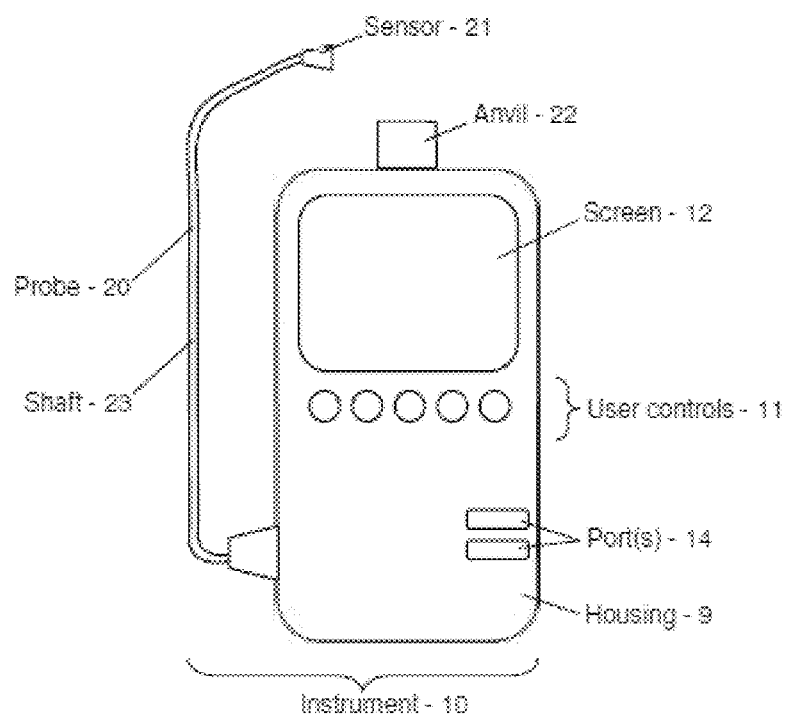
FIG. 1 is an diagram of an instrument suited for practicing the teachings herein.

In the description of embodiments presented herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Disclosed herein are methods and apparatus that provide for rapid adaptation of field use instrumentation. Specifically, the solutions provided herein enable users to rapidly adjust a combination Fourier transform infrared (FTIR) and/or Raman spectrometer that is configured for field use. Advantageously, the solutions provide for context-based configuring that corresponds to a given type of threat (analysis profile). Before discussing the solutions and depth, aspects of the instrumentation are introduced.

Referring now to FIG. 1, there is shown an exemplary instrument 10. In this non-limiting example, the instrument 10 provides a user with extensive capabilities for field-based sample analysis. Generally, sample analysis is performed by spectroscopy techniques or technologies. These spectroscopy techniques or technologies can include Fourier transform infrared (FTIR) spectroscopy and/or Raman spectroscopy. That is, the instrument 10 provides for collection of an infrared spectrum of absorption, emission, or Raman scattering from a solid, liquid or gas sample. The instrument 10 may also be referred to herein as a spectrometer.

The FTIR portion of the instrument 10 illuminates a sample with many frequencies of light at once, and measures how much of that beam is absorbed by the sample. Next, the beam is modified to contain a different combination of frequencies, giving a second data point. This process is repeated many times. Afterwards, a processor on board the instrument 10 takes the collected data to estimate absorption at each wavelength. Correlations between absorption data and characteristics for known materials are then made an output to the user.

The Raman scattering portion of the instrument 10 also illuminates the sample with a beam of light. When photons are scattered from an atom or molecule in the sample, most photons are elastically scattered (Rayleigh scattering), such that the scattered photons have the same energy (frequency and wavelength) as the incident photons. However, a small fraction of the scattered photons are scattered by an excitation. These Raman scattered photons have a frequency different from, and usually lower than, that of the incident photons. In a sample, Raman scattering can occur with a change in energy of a molecule due to a transition. The instrument 10 provides resources for collecting an optical signal associated with the Raman scattering, comparing the optical signal with data tables, and outputting correlations to the user.

In the exemplary embodiment depicted in FIG. 1, the instrument 10 is provided as a handheld device. The instrument 10 is contained within a housing 9. In this embodiment, the housing 9 is "ruggedized." That is, the housing 9 is configured with features to provide for survival in a harsh environment. Exemplary features for survival include a jacket of material to protect the exterior of the instrument 10. The jacket of material may additionally be interchangeable (for example to maintain hygiene of the instrument 10). Additionally, components within the housing 9 may be shock mounted, surface mounted or otherwise configured to withstand impact. The housing 9 may further be configured to be moisture resistant, waterproof and/or to withstand chemical degradation (such as to withstand acidity or alkalinity). For example, the instrument may be certified to MIL-STD 810G for ruggedness.

The instrument 10 includes a variety of components for enabling sampling, processing, and appropriate outputting of data and/or results. For example, the user is provided with various user controls 11. Generally, the user controls 11 enable user control of the instrument 10 for initiation of sampling, processing, and communications. Additionally, the user controls 11 enable the user to configure the instrument 10, monitor health of the instrument 10 and to perform other similar tasks. In some embodiments, the user controls 11 may be configured for a particular sampling routine or the like. Generally, the housing 9 and the user controls 11 are sealed from the environment such that the instrument will not be contaminated with sample materials or subjected to the hazards associated with a given sample.

At least one screen 12 may be provided with the instrument 10. Generally, the screen 12 provides the user with dynamic output. The output may include configuration information, status of the instrument 10, semantic information (such as date, time, location information, etc, . . . ), as well as sample analysis information and any other information deemed appropriate. In some embodiments, the screen 12 is provided as a touch sensitive screen to enable user input through the screen 12. In an exemplary embodiment, the screen 12 is provided as a liquid crystal display (LCD) with a capacitive overlay to enable touch capabilities.

In the exemplary embodiment, instrument 10 includes a sampling probe 20 as well as an anvil 22. Generally, the sampling probe 20 includes a flexible shaft 23 and at least one sensor 21. However, the probe 20 and sensor 21 may be integrated into the housing 9 in an embodiment without shaft 23, and thus provide for "point and shoot" style of sample analysis. At least one source of narrowband illumination (not shown) and at least one source of wideband illumination (not shown) may be integrated into the instrument 10, and may be used with the probe 20 and the anvil 22. In some embodiments, the anvil 22 is motorized. In some embodiments, the shaft 23 is disposed so that the probe 20 can be positioned to interrogate the sample while it is in contact with the collection optics associated with the anvil 22. In this way, a sample can be interrogated by both the Raman spectrometer and the Fourier Transform Infrared spectrometer simultaneously and/or while in a single location.

The at least one source of narrowband illumination may include, for example, at least one light emitting diode (LED) and/or laser. The at least one source of wideband illumination may include, for example, at least one electrically resistive filament and/or membrane. The source of illumination may further include optical filtering and other components as desired for producing optical effects. The instrument 10 may be further configured to work with external (independent) sources of illumination. Further, the instrument 10 may be configured to control the illumination with respect to sampling. For example, the instrument 10 may be configured to change between sources of illumination to provide adjustments to wavelengths used to illuminate a given sample. Generally, control of the source of illumination in conjunction with sampling is provided through system software.

Generally, the instrumentation includes at least one port 14. The port 14 may include a network interface such as an Ethernet, serial, parallel, 802.11, USB, Bluetooth or other type of interface (not shown). The port 14 may be used to provide for remote control, communication of data, receipt of output, shared processing, system backup, and other similar tasks. In some embodiments, the port 14 provides an interface to an external computer (such as a personal computer (PC)). When the instrument 10 is connected to a PC (not shown), software installed on the PC may be used for control and enable rapid configuration of the instrument 10. As a matter of convention, software installed on an external unit (such as a PC configured to provide users with improved access and/or control of the instrument) may generally be referred to as a "profile manager."

Generally, the instrument 10 includes an internal power supply (e.g., a battery), memory, a processor, a clock, data storage, and other similar components (not shown). Other output devices may further include a speaker (not shown), such as one configured to provide auditory output such as an alarm. Additional input devices may include a microphone (not shown), such as one configured to receive voice commands from the user.

Generally, the processor is configured to receive input from user controls 11 and to control the radiation sources, detection systems and analysis components. Accordingly, the processor will also provide appropriate information to the output. The instrument 10 may be configured to take advantage of robust processing capabilities, and may therefore include data libraries, substantial memory for data storage, calibration libraries and the like. User controls 11 may include a trigger or other such device to provide for initiation of sampling and analysis with the spectrometer 10. The output may provide raw data, spectral data, concentration data and other appropriate forms of data.

Generally, the processor is configured to execute application-specific software. That is, the processor is configured to retrieve machine executable instructions stored in machine readable media (such as in the memory or the data storage) and provided for enabling the instrument 10 to perform a selected method for operation. It should be considered that any software provided with the instrument 10 may additionally include data tables, subroutines, links to external resources, and other components as necessary or as deemed appropriate for enabling operation. As one example, the instrument 10 may include at least one library. The at least one library may include substantial chemical data. More specifically, for any given chemical, compound, element or other type of material, the library may include information such as spectral properties, identity, dangerous good classification (NFPA labeling) information, material safety data sheet (MSDS) information and the like. As another example, the instrument 10 may include language libraries for configuring a user interface according to a language of the user.

As may be surmised, the instrument 10 provides a versatile system. Part of the versatility is realized by the complexity of the instrument 10. By virtue of the complexity of the instrument 10, it is possible to configure the instrument 10 for improved performance. That is, aspects such as analysis time, order of analyses, power levels and the like may be configured into specific response profiles according to types of analyses, such as analysis of industrial chemicals, homemade explosives, a clandestine drug lab, street narcotics, or chemical warfare agents. More specifically, appropriately adjusting a number of system parameters for the instrument 10 will improve precision and accuracy for given types of analysis.

Figure 2:
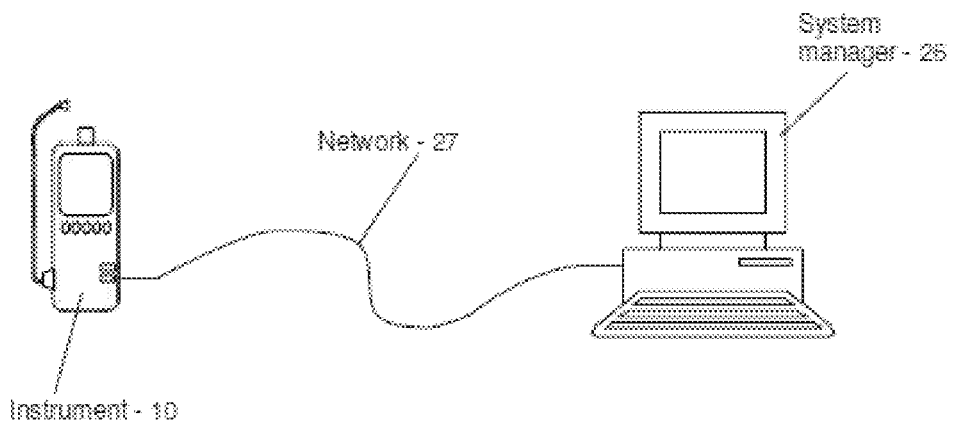
FIG. 2 is an illustration of components for setting up and managing the instrument of FIG. 1.

Aspects of an exemplary system for configuring the spectrometer 10 are provided in FIG. 2. Referring to FIG. 2, there are shown aspects of a system for configuring the spectrometer 10. In this exemplary embodiment, a system manager 26 is configured to communicate with and control the instrument 10. The system manager 26 communicates with the instrument 10 through network 27. Network 27 may take advantage of any type of communications protocol deemed appropriate, such as the types of communication discussed above.

Generally, the system manager 26 is provided as machine executable instructions stored on machine readable media (that is, as "software" that may be executed on a computer, such as a personal computer (PC)). In some embodiments, the system manager 26 provides users with substantial information from the instrument 10. For example, the system manager 26 can be configured to display at least some of to all of the internal parameters of the instrument 10. The system manager 26 can further allow a user to edit at least some of the internal parameters of the instrument 10. Editing of parameters can be performed in a variety of different ways. For example, the instrument 10 can make use of a configuration data file, read only memory (ROM), and other similar techniques as may be known in the art. In some embodiments, the system manager 26 can be provided as machine executable instructions stored on machine readable media, that is, as "software" that can be executed on the instrument 10.

The system manager 26 (as well as an on-screen user interface of the instrument 10) can be provided in a variety of different manners. For example, user interface schemes can include a graphical user interface (GUI), a text-based interface, and can include files configured for transfer to another application.

In some embodiments, certain parameters are set in one way for a given user or situation, and another way for a different user or situation. Accordingly, the instrument 10 can be configured with various profiles and/or accounts. A system administrator making use of the system manager 26 is provided with resources to effectively and conveniently manage the diverse users, accounts and system settings.

For example, it is recognized that there are various stages for use of or interaction with the instrument 10. More specifically, in a first stage, global settings of the instrument 10 are configured. In a second phase, a user will configure the instrument 10 for a given surveillance. In the third phase, the user will commence surveillance by analyzing samples. In a last phase, the user (and/or another party) will review and/or analyze data from sample surveillance. Reference may be had to FIG. 3.

FIG. 3 provides an illustration of the stages of use of the instrument 10. Additionally, FIG. 4 is a table depicting considerations for a user to evaluate when configuring the instrument 10 for surveillance.

In order to efficiently manage setup of the instrument 10, the system manager 26 includes software that provides for context-based configurations. That is, embodiments of the instrument 10 provide users with an interface that provides for selecting a configuration that is most appropriate for a given situation.

As discussed herein, a context-based configuration may be referred to as a "response profile." By using response profiles, a diversity of users may use the instrument 10 with relatively little time spent on instrument set-up or maintenance. This is particularly advantageous where diverse users may pass the instrument 10 from one to another during an emergency situation.

Generally, the instrument 10 stores a plurality of response profiles in data storage and/or memory. Each response profile may be configured well in advance of use, and under controlled conditions. For example, during instrument set-up and/or calibration an instruments technician (or engineer, or any other similarly situated party) may determine appropriate settings for a variety of parameters for any given type of analysis. As discussed above, the system manager 26 may be used to establish and/or maintain response profiles stored in the instrument 10.

Accordingly, users are provided with an instrument that is reconfigurable "on the fly." This means that the bomb disposal department may use the instrument 10 one day and the hazardous materials response team may use the instrument 10 the next day. In some cases, these are the same team. In any case, the product will allow them to select the configuration associated with their type of call and the instrument will be ready to go.

Editing of each response profile may be done on the instrument as well as through the profile manager. Users can also export profiles to an external data storage medium and import it onto another instrument. Users are able to add, delete, and edit the settings on profiles as well as change the profile button icon. An administrator has the ability to restrict some of the profile settings to correspond to department safety or procedural policies.

Figure 5:
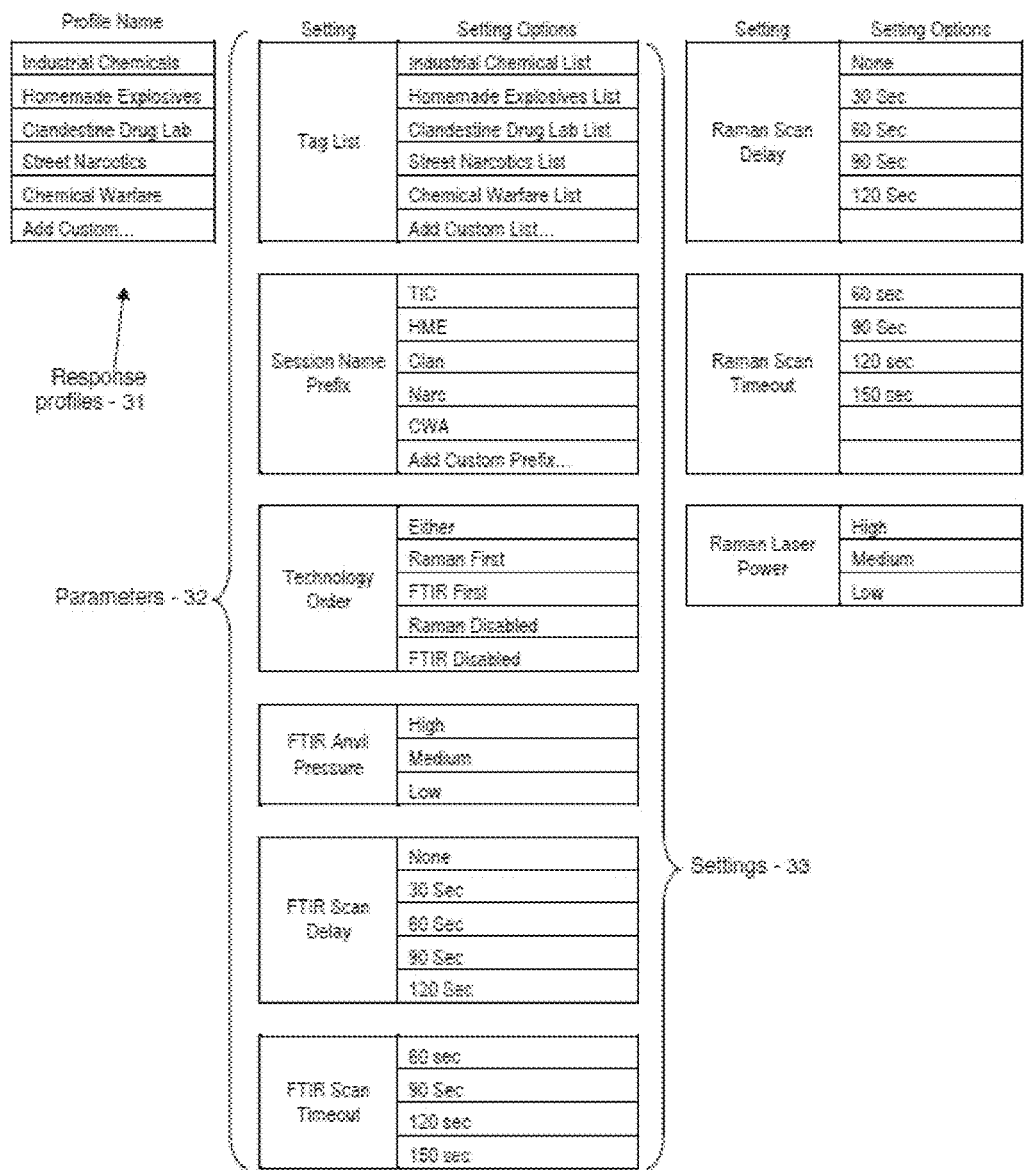

Refer now to FIG. 5, where aspects of a plurality of response profiles 31 are depicted. As shown in this example, each response profile 31 may be given an appropriate name such that users may make expedient choices for configuring the instrument 10. In this example, the response profiles include profiles for: industrial chemicals, homemade explosives, a drug laboratory, street narcotics, and chemical warfare. Additionally, a user may want to add a custom response profile 31 and may be presented with this option. In some embodiments, the user may copy an existing response profile 31, slightly modify the respective response profile 31, and then save the modified response profile 31 as a new response profile 31. For example, a user may decide to modify duration of analyses based on concentrations of compounds encountered in the field.

Each response profile 31 includes a plurality of parameters 32. Each parameter 32 is assigned a particular setting 33, or "value." Parameters 32 may include, by way of example and without limitation, a tag list (such as a particular name to be assigned to a given sample), a session name (such that upon subsequent review of data, a reviewer may identify settings for each parameter 32), a technology order (a priority of processing, such that order of processing or sample analysis is controlled), instrument pressure (such as for the anvil 22), Raman laser power (such as for sampling temperature sensitive or explosive materials), and a plurality of temporal parameters (such as for scan duration, scan delay, scan timeout and the like).

As one may surmise, a great number of parameters 32 may be adjusted to provide for each response profile 31. The response profiles 31 and parameters 32 shown in FIG. 5 are merely illustrative and are not limiting of the teachings herein.

Advantageously, the teachings herein provide for combined functionality of handheld FTIR spectroscopy with handheld Raman spectroscopy. This includes reduction in size and weight (and cost) of the single unit over the combination of two units. Further advantages include the opportunity to tailor software workflows. Additionally, sample surveillance may be substantially expedited. For example, the Raman probe may be designed to be positioned to interrogate the sample while it is in the same location as for FTIR sampling. That facilitates remote operation of the instrument using both methodologies, which is particularly important in field applications when samples may be explosive or are otherwise very hazardous.

These tools have seen increasing adoption for field-based assessment by diverse users including military, emergency response, and law enforcement.

Frequently, end-users of portable devices are non-scientists who rely on embedded software and the associated algorithms to convert collected data into unambiguous actionable information.

One class of problems commonly encountered in field applications is identification. Identification algorithms are designed to mine a library of known materials and determine whether the unknown measurement is consistent with a stored response, or combination of stored responses. Such algorithms can be used to identify a material from many thousands of possible candidates.

A second class of problems is screening. Screening algorithms evaluate whether at least a subset of features in an unknown measurement correspond to one or more specific substances of interest and are typically configured to evaluate candidates from a small list of potential target analytes. As such, screening algorithms are less broadly applicable than identification algorithms; however, they typically provide faster detection rates which makes them attractive for specific applications such as chemical warfare agent or narcotics detection.

Recently, a new approach called tagging has been developed, which is a merging of a screening capability within an identification algorithm framework. Tagging maintains a broad identification capability that field users demand (an ability to identify thousands of possible pure materials and trillions of potential mixture candidates), while simultaneously providing an extended capability that allows users to configure their own tag list (e.g. a user defined set of test targets, also called a watchlist) for enhanced detection of target substances. Given that the list can be rapidly configured in the field, tagging provides users the ability to incorporate their situational awareness into the sample assessment provided by the device. As discussed herein, higher detection rates and lower limits of detection can be achieved when items are tagged. Additionally, when identified, tagged items can be preferentially displayed in the device graphical user interface (GUI) to provide an unambiguous indication to the user that a substance of interest has been detected.

Some embodiments described herein are generally directed to an overview and performance characterization of a combined identification/screening algorithm. The combined algorithm provides enhanced detection capability more typical of screening algorithms while maintaining a broad identification capability. Additionally, this approach can enable users to incorporate situational awareness during a response.

Algorithm Overview

Computational Considerations

As discussed above, contemporary handheld analyzers are increasingly capable of automatically identifying both pure materials and mixtures. Analysis of unknown mixtures presents special computational challenges that cannot be ignored. Modern reference databases frequently contain in excess of 10,000 library spectra, and some mixture algorithms deployed on handheld devices attempt to simultaneously fit up to 5 mixture components. The number of potential mixture solution candidates that can be evaluated for a given library can be calculated using the following formula:

$$N = \frac{n!}{k!(n-k)!} \quad (1)$$

where N is the number of possible mixture candidates, n is the number of library reference spectra, and k is the maximum number of mixture components that are simultaneously fit. Based on the formula shown above, the number of possible mixture combinations scales rapidly with the number of components that are simultaneously fit, especially for large reference library databases. To illustrate this point, Table 1 captures the number of possible mixture candidates for a reference library containing 10,000 items when 2-5 component solutions are considered.

TABLE 1

Number of potential mixture candidates (N) as a function of the number of mixture components fit (k) for a 10,000 item library

| n | k | N |
| --- | --- | --- |
| 10,000 | 2 | $4.9995 \times 10^7$ |
| 10,000 | 3 | $1.6662 \times 10^{11}$ |
| 10,000 | 4 | $4.1642 \times 10^{14}$ |
| 10,000 | 5 | $>1 \times 10^{15}$ |

It can be seen from Table 1 that with a 10,000 item library, there are almost 50 million possible two component mixture candidates alone. Further complicating the issue is that handheld devices typically have limited on-board computing power. With the on-board processing capability available on portable devices today, it would take days to evaluate every potential mixture solution that could be generated from a large, modern reference database. As a result of the computational expense associated with the mixture problem, it is common for handheld identification devices to incorporate a rapid calculation that can be used to down select the library to a reduced and therefore more manageable number of entries. The down selection is a preliminary step performed prior to final analysis by more precise pure component and mixture analysis algorithms.

Figure 6:
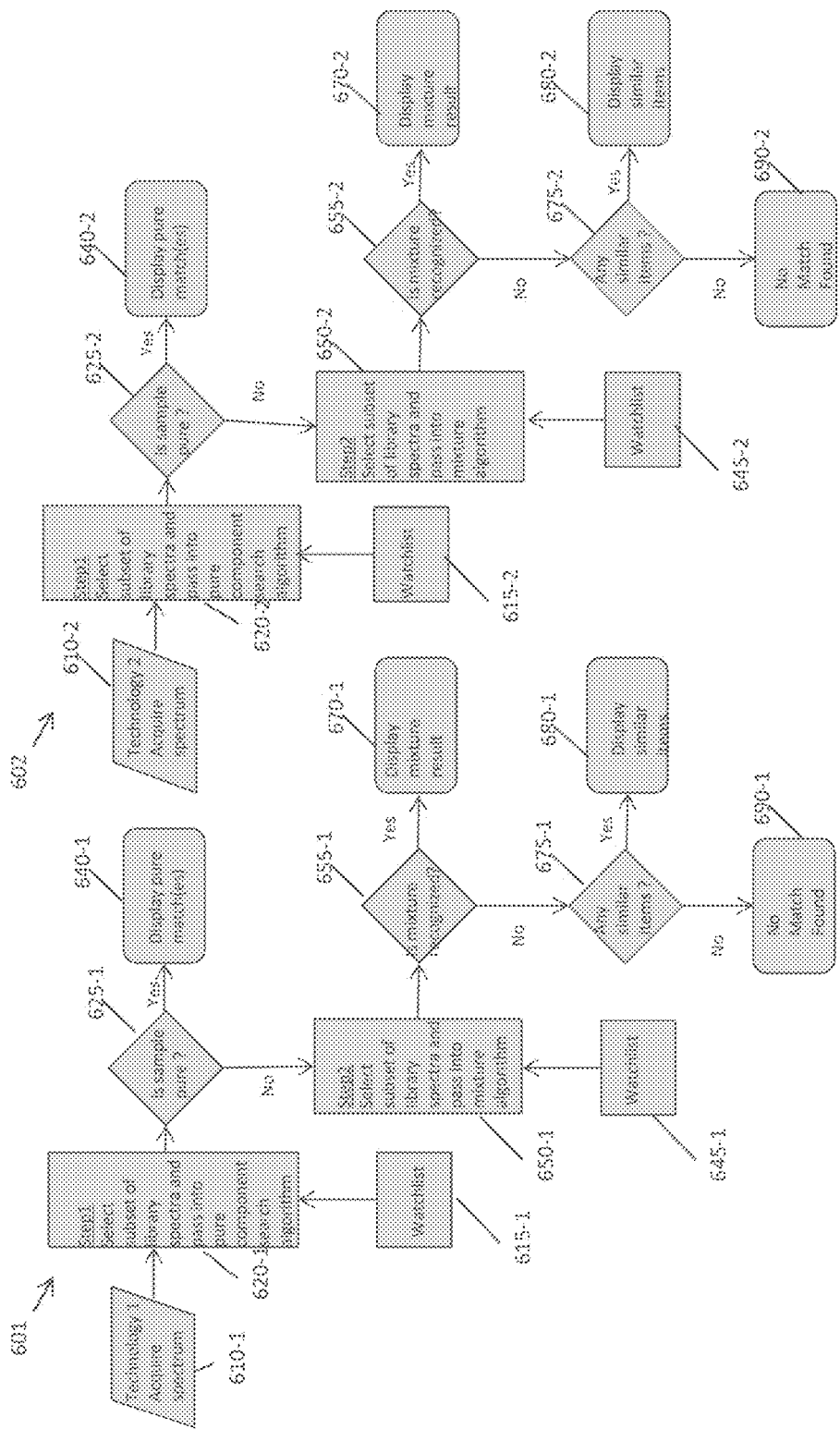
FIG. 6 is a flow chart showing a high level overview of the logic used on a spectrometer (two separate technologies without data fusion).

Shown in FIG. 6 is a flow chart illustrating an exemplary high level overview of an identification algorithm used in a handheld identification device without data fusion, that is, without integration of spectral information from different technologies. Further description of such an identification algorithm can also be found in U.S. Pat. No. 7,254,501, entitled: "SPECTRUM SEARCHING METHOD THAT USES NON-CHEMICAL QUALITIES OF THE MEASUREMENT," issued to Brown et al., and assigned to the assignees of the present application, the disclosure of which is hereby incorporated by reference in its entirety. However, where anything in the incorporated reference contradicts anything stated in the present application, the present application prevails. As noted in the flow chart, down selection is performed prior to pure component assessment and mixture analysis. The intention of this approach is to enable rapid analysis times for end users and ensure that the majority of computational time is allotted to making a detailed assessment of the unknown sample against select library items of interest.

While optimized for computational efficiency, the down selection procedures are also designed to retain reference library candidates most likely to be present in the unknown spectrum. The down selection strategy is not lossless, however, so it is possible for items that are present in the unknown sample to be omitted from consideration prior to analysis by the final algorithms. For pure materials this is rarely an issue; however, this does become more of a difficulty for minor mixture components whose features in the unknown spectrum may be largely masked by the dominant mixture component(s). One aspect of the enhanced screening capability provided by tagging is to reduce the likelihood that a tagged substance (i.e., a substance included on a watchlist) will be erroneously dismissed from consideration prior to the final analysis algorithms. Further description of tagging can also be found in U.S. patent application Ser. No. 13/540,152, entitled: "METHOD FOR TAGGING REFERENCE MATERIALS OF INTEREST IN SPECTROSCOPIC SEARCHING APPLICATIONS," to Green et al., and assigned to the assignees of the present application, the disclosure of which is hereby incorporated by reference in its entirety. However, where anything in the incorporated reference contradicts anything stated in the present application, the present application prevails.

In the flow chart shown in FIG. 6, two methods 601 and 602 of determining the most likely composition of a sample by at least two technologies (e.g., FTIR as Technology 1 and Raman as Technology 2) using a spectrometer include at step 610-1 obtaining data from the sample by a first technology (Technology 1) using the spectrometer, wherein the data comprises a first representation of a measured spectrum obtained by the first technology, and at step 610-2 obtaining data from the sample by a second technology (Technology 2) using the spectrometer, wherein the data comprises a second representation of a measured spectrum obtained by the second technology. The methods then include at steps 620-1 or 620-2 (for the first or second method 601 or 602, respectively) determining a precision state of the first or second representation of the measured spectrum, providing a first or second set of library candidates and, for each library candidate, providing data representing each library candidate, wherein the data comprises a representation of a library spectrum obtained by the first or second technology, selecting a first or second subset of library candidates by determining a first or second representation of the similarity of the sample to each library candidate in the first or second set of library candidates using (i) the first or second representation of the measured spectrum, (ii) the precision state of the first or second representation of the measured spectrum, (iii) the representation of the library spectrum for that library candidate, and (iv) the precision state of the representation of the library spectrum for that library candidate, and determining a first or second most likely composition of the sample based upon the selected first or second subset of library candidates. The methods 601 and 602 can optionally include, at steps 615-1 or 615-2, adding a first or second watchlist of library candidates to the first or second subset of library candidates.

The critical question to be answered by the spectral library search appliance is: given the instrumental measurement of the specimen, and the conditions under which it was measured, (1) is it probable that any of the library records are a match?, and (2) what are the probabilities PA, PB . . . that the measured material is in fact A, B, etc.? These probabilities must be directly dependent on the measurement data, and its quality. Generally speaking, the measurement quality is a function of the accuracy of the measurement and its precision (or variability). It can often be assumed that, if the instrument has been designed appropriately and/or appropriate signal conditioning methods have been used, the measurement will be reasonably accurate, but inevitably suffers from imprecision to a degree dependent on the measurement conditions.

The method collects data and measures sources of uncertainty. For a dispersive Raman spectrometer measurement using charge coupled device (CCD) detection, as an example, many distinct sources of variability contribute to $\Sigma_{meas}$, the precision state of the measurement:

$$\Sigma_{meas} = f(I_{Ral}, I_{Ram}, I_{fl}, I_{ambient}, I_{dark}, \sigma_{read}, Q, D_{CCD}, G_{CCD}, C, T, H, t, L) \quad (2)$$

where $I_{Ral}$ is the Raleigh scatter intensity, $I_{Ram}$ is the Raman scatter intensity, $I_{fl}$ is the fluorescence intensity, and $I_{ambient}$ is the ambient light intensity.

All of the terms listed in Eq. 2 affect the uncertainty of the analytical measurement because they each contribute photon shot noise $I_{dark}$ is the dark current intensity in the CCD, the spontaneous accumulation of detector counts without impinging photons, which also contributes shot noise, $\sigma_{read}$ is the read noise (imprecision in reading out the CCD response), Q is quantization error (a consequence of the analog-to-digital conversion ADC), $D_{CCD}$ is a term relating to variability that is a consequence of detects in the CCD construction, $G_{CCD}$ is the gain on the CCD (the conversion factor from electrons to counts), T and H are the temperature and humidity conditions of the measurement, t is the time spent integrating the signals, C is physicochemical effects that can alter the exact Raman intensities of the sample (note that each of these effects has a potential wavelength dependence), and L is a "long-term" variability term that reflects changes in the system performance over a time period greater than that of any individual sample measurement, e.g., calibration related variability. As is apparent from the above discussion, some sources of imprecision are determined by the measurement conditions (e.g., photon shot noise, dark noise), some are determined by the unit taking the measurements (e.g., system gain, read noise, quantization noise), and some are determined by the overall design of the platform (e.g., wavelength axis and linewidth stability, temperature/humidity sensitivity).

Once the scan data arrives at a signal-to-noise-ratio (SNR) threshold deemed sufficient for this chemical identification, the result is the identification of chemical X. The null hypothesis states that the measurement spectrum belongs to the population of the reference library spectrum given the measurement uncertainty. The alternative hypothesis states that the measurement spectrum does not belong to the population of the reference library spectrum.

In statistics, the p-value is the probability of obtaining the observed sample results (or a more extreme result) when the null hypothesis is actually true. If this p-value is very small, usually less than or equal to a report threshold value previously chosen called the significance level (traditionally 95%), it suggests that the observed data is inconsistent with the assumption that the null hypothesis is true, and thus that hypothesis must be rejected. Thus, if a p-value (herein also called a report threshold value) is greater than or equal to 0.05, the measurement is considered consistent with the reference spectrum and the device will report a positive match (e.g., by displaying a green screen). Otherwise, the device may undertake mixture analysis, or will report similar items, as described below, or will report no match depending on the unit configuration.

If at step 625-1 or 625-2 the sample is a pure sample, determined as described further below, then step 640-1 or 640-2 displays the pure match, or, if the pure match chemical is known by more than one name, then step 640-1 or 640-2 displays the pure matches. If at step 625-1 or 625-2 the sample is not a pure sample, that is, if the similarity of the sample to any single library candidate is less than a report threshold value, which, as described above, can be greater than or equal to 0.05, then the methods 601 and 602 further include at steps 650-1 or 650-2 selecting a third or fourth subset of library candidates by determining a third or fourth representation of the similarity of the sample to a mixture of library candidates in the first or second subset, respectively, of library candidates using (i) the first or second representation of the measured spectrum; (ii) the precision state of the first or second representation of the measured spectrum; (iii) the representation of the library spectrum for that library candidate; and, optionally, (iv) the precision state of the representation of the library spectrum for that library candidate. Determining the resulting most likely composition of the sample is based on the determined representations of similarity of the sample to the mixture of library candidates, that is, based on a determination that the similarity of the sample to a mixture of library candidates is greater than a report threshold value, which, as described above, can be greater than or equal to 0.05. The methods 601 and 602 can optionally include, at steps 645-1 or 645-2, adding a third or fourth watchlist of library candidates to the third or fourth subset of library candidates. At step 655-1 or 655-2, if the mixture is recognized (p-value greater than or equal to 0.05), then step 670-1 or 670-2 displays the mixture result. If the mixture is not recognized, then at step 675-1 or 675-2, if there are any similar items, that is, any items resulting in a p-value greater than $1 \times 10^{-4}$ and less than 0.05, then step 680-1 or 680-2 displays the similar items. If there are no similar items, then step 690-1 or 690-2 reports no match found.

Reporting Considerations

A final topic not explicitly shown in FIG. 6 is the reporting criteria associated with automated mixture algorithms. For the analysis to be truly automated, goodness of fit thresholds must be set in the algorithm to determine which component(s), if any, will be reported. The need to set reporting thresholds is universal and does not depend on the type of analysis algorithm that is used.

Selection of the reporting threshold value has a direct impact on the tradeoff between true positive rate (TPR) and false positive rate (FPR) of the search appliance. In a typical unknown identification scenario, such as a hazardous material identification (e.g., a hazmat call), special consideration is made to ensure that the FPR is kept low. This prevents the user from acting on information that may be ambiguous and allows them to focus time and efforts on other assessments that may provide more definitive information. By contrast, in a screening scenario, the reporting thresholds are often set to maximize TPR, even at the expense of a higher FPR. This is because in screening scenarios, such as medical diagnostic testing, there is often a second confirmatory test that can be performed in order to mitigate false positives.

Based on these considerations, another reason that screening algorithms are capable of providing better detection rates than standard identification algorithms is that the reporting thresholds are optimized for substances of interest. Optimization of the reporting thresholds for tagged items is expected to result in a much better detection capability, although a slight increase in false alarm rate may be expected as well.

Field Considerations

End users of identification equipment frequently have information available to them from a variety of sources. During a typical response, information in the form of other external data intelligence may be available in the form of product labels, sample observations (solid, liquid, or gas, color, odor), pH measurements, and test results from a variety of analyzers. As users begin to evaluate all of the information available to them, they make assessments about what potential materials are most likely to be present in the unknown sample. Traditional identification equipment and algorithms have no way of incorporating real time information, or situational awareness, into the identification assessment provided by the device. As demonstrated above, the tagging approach provides higher detection rates and lower limits of detection than a typical 'blind' identification algorithm. Since the instrument is designed so that the tag list (i.e., the watchlist) can be adapted, modified, or edited at any time, the tagging method provides a novel capability for instrument operators to better incorporate knowledge gained during the course of a response.

Figure 7A:
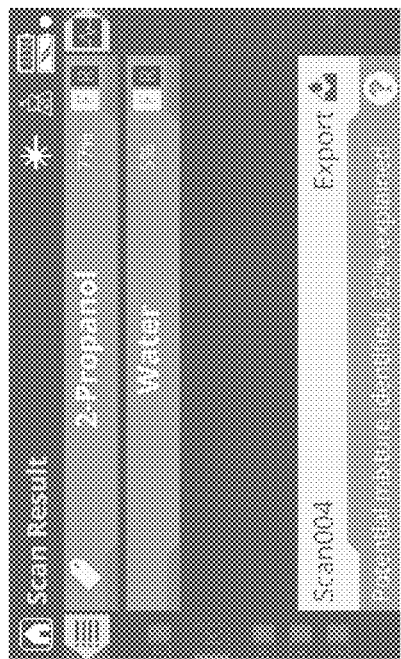
FIGS. 7A-7B are illustrations of exemplary result screens highlighting the display of tagged items, here showing 2-propanol in a pure component match (FIG. 7A), and a mixture match (FIG. 7B).
Figure 7B:
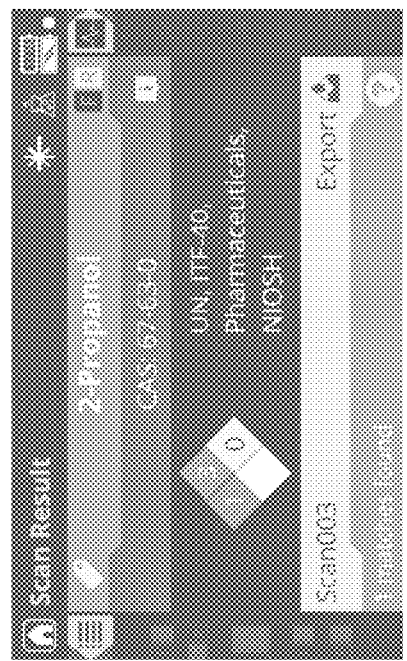

Another benefit of tagging is that when tagged items are identified, the tagged items can be displayed to the user with an icon next to them, providing an unambiguous indication to the end user that a substance of interest has been identified. To ensure that the tag icon is obvious to the end user, mixtures can be displayed with tagged substances appearing at the top, regardless of the spectral contribution (e.g., weight) for that substance. FIGS. 7A and 7B show example result displays for a pure component match (FIG. 7A), and a mixture match (FIG. 7B). The respective matches can be highlighted in a variety of ways, such as using different color screens.

While the focus herein has been most heavily on the enhanced detection capabilities that tagging provides, the GUI elements described herein provide substantial benefits in their own right. For many applications, the threat landscape is constantly expanding or changing. As a result, it becomes difficult for end users to keep abreast of new substances of interest and there may be uncertainty regarding which substances are of most concern. With tagging in place, users no longer need to remember a long list of threat materials to watch for. Instead, they are trained that any result showing a red flag warrants escalation.

Data Fusion

As has been described above, a screening algorithm termed 'tagging' has been deployed onto handheld identification devices, such as spectrometers. This concept can also be deployed on a spectrometer that combines two or more technologies. In the first instance, a profile can be setup on the device.

The profile can include several settings:
Raman laser power,
Raman scan delay,
Raman scan timeout,
FTIR anvil force,
FTIR scan delay,
FTIR scan timeout, and
a tag list of items relevant to the profile.

A tag list (also called a watchlist herein) of items can be of any technology; in the case described herein, the two technologies are Raman and FTIR spectroscopy. By selecting a chemical in the library, that chemical, whether Raman only, FTIR only or covered by both technologies, will be searched when a scan of that technology is performed. Examples of pure chemicals include explosive materials, such as triacetone triperoxide (TATP), RDX, and hexamethylene triperoxidediamine (HMTD), toxic materials, such as acrolein, chlorosulfonic acid, isopropyl isocyanate, and toluene 2,4-diisocyanate, and narcotic materials, such as heroin HCl, cocaine freebase, methamphetamine HCl, and JWH-018. Examples of mixtures of chemical include cocaine HCl/benzocaine, heroin HCl/acetaminophen (common narcotic mixtures), 2-propanol/methanol, ethanol/water, methyl ethyl ketone/isopropanol/ethanol, and acetaminophen/a-Lactose monohydrate. FIG. 6 illustrates the data flow of two separate technologies, that could be two completely separate devices or technologies where no a priori knowledge is passed into the decision engine for either technology, both operating completely separately.

A significant possibility when two technologies are combined into the same device, is the possibility to share information between them. Two possibilities described below are 1) to pass information before, and 2) after a measurement.

Before (Pre-Data Collection)

Figure 8:
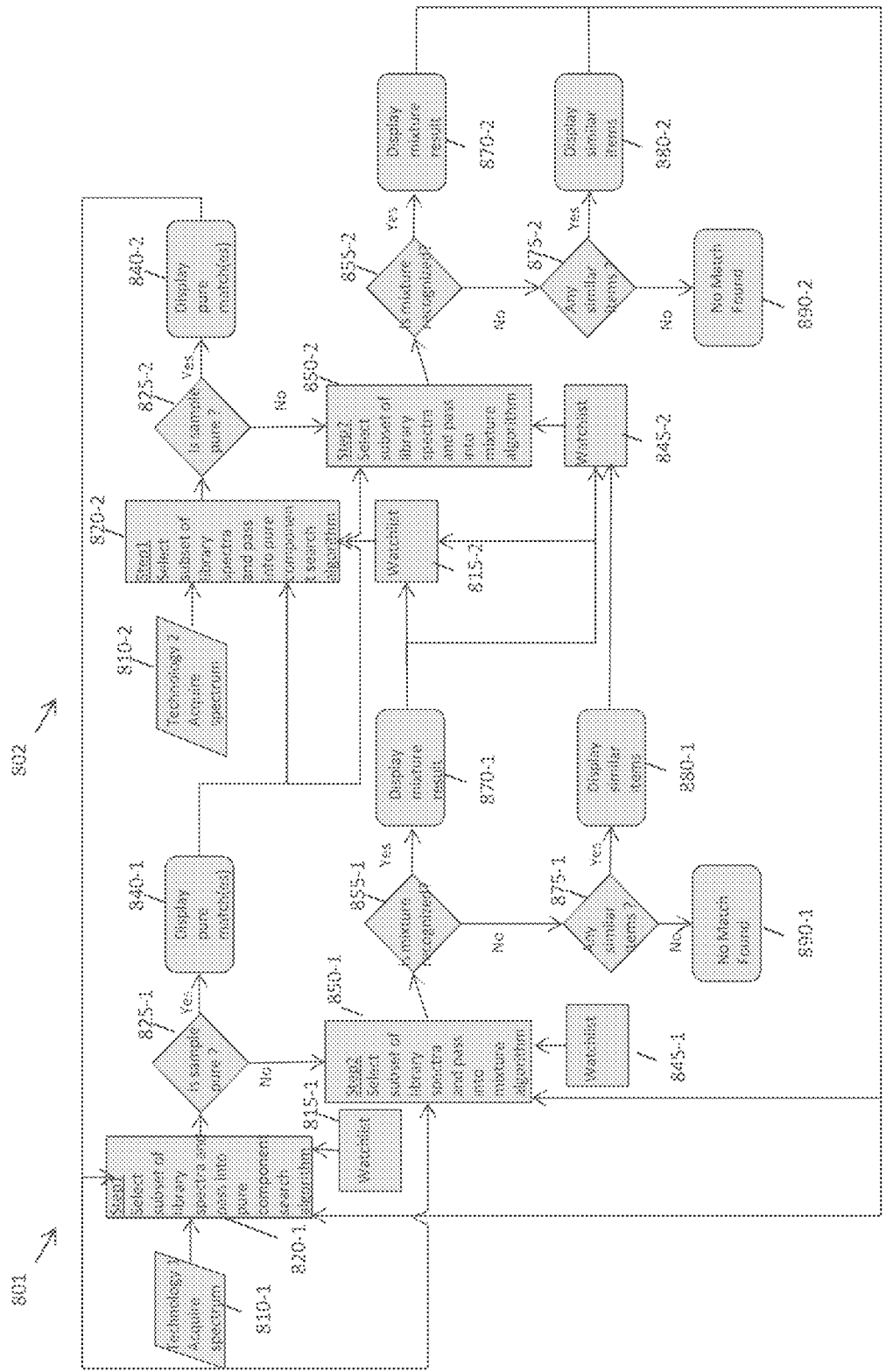
FIG. 8 is a flow chart showing a high level overview of the logic used on a spectrometer with two separate technologies and including data fusion.

In the first instance, the possibilities encountered when passing information obtained from a first technology before a scan has been initiated by a second technology are considered. In FIG. 8, the flow of collecting data using one technology is described. When Technology 1 has given a result, those identifications are passed into the subset of data for consideration by Technology 2, that is those items are considered in the same manner as tagging, but have resulted from an identification by Technology 1.

In the flow chart shown in FIG. 8, two methods 801 and 802 of determining the most likely composition of a sample by at least two technologies (e.g., FTIR as Technology 1 and Raman as Technology 2) using a spectrometer and including data fusion include at step 810-1 obtaining data from the sample by a first technology (Technology 1) using the spectrometer, wherein the data comprises a first representation of a measured spectrum obtained by the first technology, and at step 810-2 obtaining data from the sample by a second technology (Technology 2) using the spectrometer, wherein the data comprises a second representation of a measured spectrum obtained by the second technology. The methods then include at steps 820-1 or 820-2 (for the first or second method 801 or 802, respectively) determining a precision state of the first or second representation of the measured spectrum, providing a first or second set of library candidates and, for each library candidate, providing data representing each library candidate, wherein the data comprises a representation of a library spectrum obtained by the first or second technology, selecting a first or second subset of library candidates by determining a first or second representation of the similarity of the sample to each library candidate in the first or second set of library candidates using (i) the first or second representation of the measured spectrum, (ii) the precision state of the first or second representation of the measured spectrum, (iii) the representation of the library spectrum for that library candidate, and, optionally, (iv) the precision state of the representation of the library spectrum for that library candidate, and determining a first or second most likely composition of the sample based upon the selected first or second subset of library candidates. The methods 801 and 802 can optionally include, at steps 815-1 or 815-2, adding a first or second watchlist of library candidates to the first or second subset of library candidates.

If at step 825-1 or 825-2 the sample is a pure sample, determined as described further below, then step 840-1 or 840-2 displays the pure match, or, if the pure match chemical is known by more than one name, then step 840-1 or 840-2 displays the pure matches. In contrast to methods 601 and 602, however, the pure match, or first most likely composition of the sample displayed at step 840-1 is added to the second subset of library candidates obtained at step 820-2. Alternatively, the second most likely composition of the sample displayed at step 840-2 is added to the first subset of library candidates obtained at step 820-1.

If at step 825-1 or 825-2 the sample is not a pure sample, that is, if the similarity of the sample to any single library candidate is less than a report threshold value, which, as described above, can be greater than or equal to 0.05, then the methods 801 and 802 further include at steps 850-1 or 850-2 selecting a third or fourth subset of library candidates by determining a third or fourth representation of the similarity of the sample to a mixture of library candidates in the first or second subset, respectively, of library candidates using (i) the first or second representation of the measured spectrum, (ii) the precision state of the first or second representation of the measured spectrum, (iii) the representation of the library spectrum for that library candidate; and, optionally, (iv) the precision state of the representation of the library spectrum for that library candidate. Determining the resulting most likely composition of the sample is based on the determined representations of similarity of the sample to the mixture of library candidates, that is, based on a determination that the similarity of the sample to a mixture of library candidates is greater than a report threshold value, which, as described above, can be greater than or equal to 0.05. The methods 801 and 802 can optionally include, at step 845-1 or 845-2, adding a third or fourth watchlist of library candidates to the third or fourth subset of library candidates. In contrast to methods 601 and 602 shown in FIG. 6, however, the pure match, or first most likely composition of the sample displayed at step 840-1 is added to the fourth subset of library candidates at step 850-2.

At step 855-1 or 855-2, if the mixture is recognized, (p-value greater than or equal to 0.05), then step 870-1 or 870-2 displays the mixture result. If the mixture is not recognized, then at step 875-1 or 875-2, if there are any similar items, that is, any items resulting in a p-value greater than $1 \times 10^{-4}$ and less than 0.05, then step 880-1 or 880-2 displays the similar items. If there are no similar items, then step 890-1 or 890-2 reports no match found. In contrast to methods 601 and 602, however, the mixture result displayed at step 870-1 or the similar items displayed at step 880-1 are added to the second watchlist at step 815-2 and the fourth watchlist at step 845-2. Alternatively, the mixture result displayed at step 870-2 or the similar items displayed at step 880-2 are added to the first subset of library candidates obtained at step 820-1 or the third subset of library candidates obtained at step 850-1.

Further to this concept, information about a sample could be passed into an algorithm making decisions around which data to pass within the algorithm. A user could provide information about the physical state of the sample, such as its form (solid, liquid, or gas (e.g., in a container)), or its color. These attributes could be used to include or rule out items being considered by the algorithm.

Figure 9:
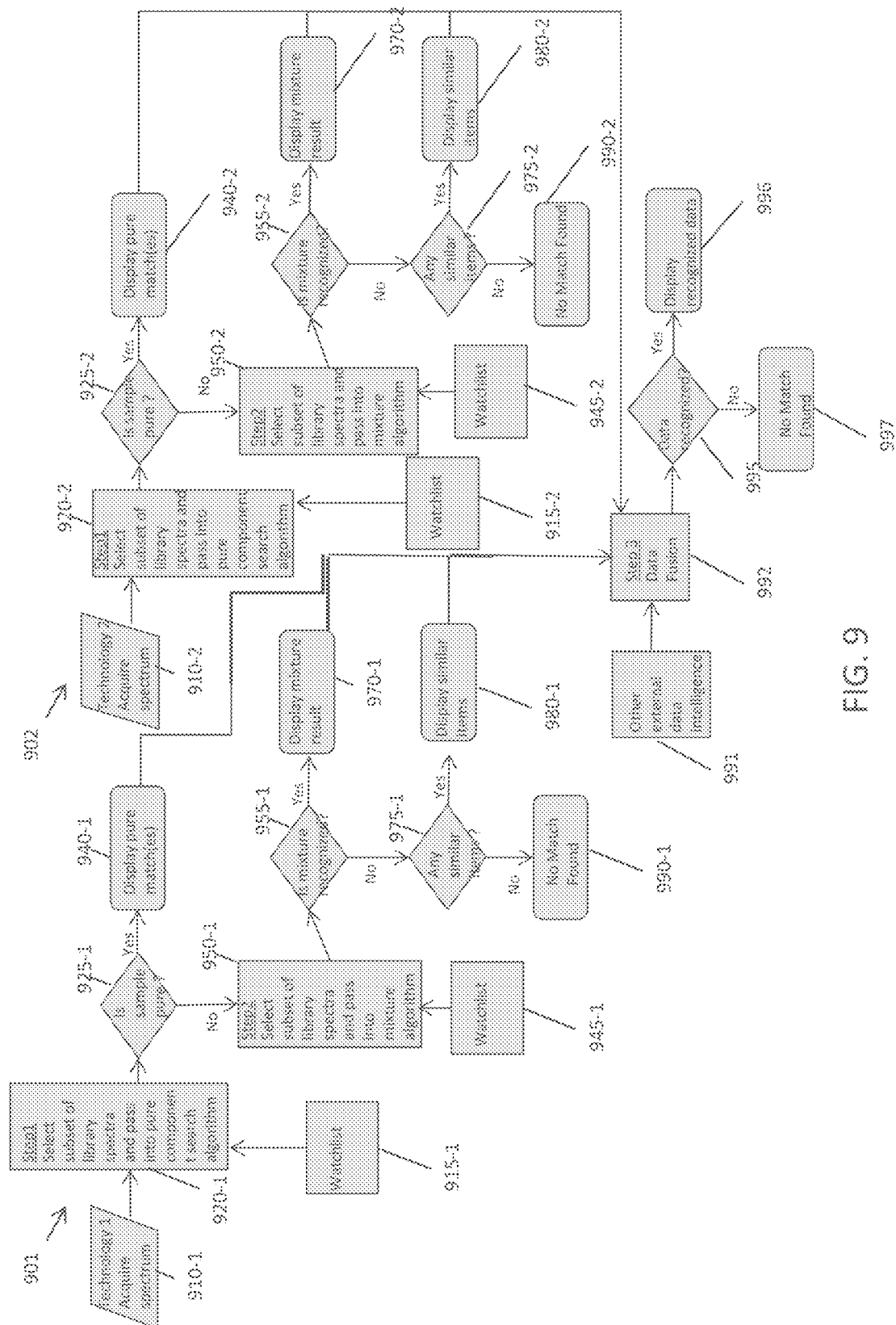
FIG. 9 is a flow chart showing a high level overview of the logic used on a spectrometer with two separate technologies, including other external data such as at least one observed property of the sample, and including data fusion.

In the flow chart shown in FIG. 9, two methods 901 and 902 of determining the most likely composition of a sample by at least two technologies (e.g., FTIR as Technology 1 and Raman as Technology 2) using a spectrometer and including data fusion include at step 910-1 obtaining data from the sample by a first technology (Technology 1) using the spectrometer, wherein the data comprises a first representation of a measured spectrum obtained by the first technology, and at step 910-2 obtaining data from the sample by a second technology (Technology 2) using the spectrometer, wherein the data comprises a second representation of a measured spectrum obtained by the second technology. The methods then include at steps 920-1 or 920-2 (for the first or second method 901 or 902, respectively) determining a precision state of the first or second representation of the measured spectrum, providing a first or second set of library candidates and, for each library candidate, providing data representing each library candidate, wherein the data comprises a representation of a library spectrum obtained by the first or second technology, selecting a first or second subset of library candidates by determining a first or second representation of the similarity of the sample to each library candidate in the first or second set of library candidates using (i) the first or second representation of the measured spectrum, (ii) the precision state of the first or second representation of the measured spectrum, (iii) the representation of the library spectrum for that library candidate, and, optionally, (iv) the precision state of the representation of the library spectrum for that library candidate, and determining a first or second most likely composition of the sample based upon the selected first or second subset of library candidates. The methods 901 and 902 can optionally include, at steps 915-1 or 915-2, adding a first or second watchlist of library candidates to the first or second subset of library candidates.

If at step 925-1 or 925-2 the sample is a pure sample, determined as described further below, then step 940-1 or 940-2 displays the pure match, or, if the pure match chemical is known by more than one name, then step 940-1 or 940-2 displays the pure matches.

If at step 925-1 or 925-2 the sample is not a pure sample, that is, if the similarity of the sample to any single library candidate is less than a report threshold value, which, as described above, can be greater than or equal to 0.05, then the methods 901 and 902 further include at steps 950-1 or 950-2 selecting a third or fourth subset of library candidates by determining a third or fourth representation of the similarity of the sample to a mixture of library candidates in the first or second subset, respectively, of library candidates using (i) the first or second representation of the measured spectrum, (ii) the precision state of the first or second representation of the measured spectrum, (iii) the representation of the library spectrum for that library candidate, and, optionally, (iv) the precision state of the representation of the library spectrum for that library candidate. Determining the resulting most likely composition of the sample is based on the determined representations of similarity of the sample to the mixture of library candidates, that is, based on a determination that the similarity of the sample to a mixture of library candidates is greater than a report threshold value, which, as described above, can be greater than or equal to 0.05. The methods 901 and 902 can optionally include, at step 945-1 or 945-2, adding a third or fourth watchlist of library candidates to the third or fourth subset of library candidates, respectively.

At step 955-1 or 955-2, if the mixture is recognized, (p-value greater than or equal to 0.05), then step 970-1 or 970-2 displays the mixture result. If the mixture is not recognized, then at step 975-1 or 975-2, if there are any similar items, that is, any items resulting in a p-value greater than $1 \times 10^{-4}$ and less than 0.05, then step 980-1 or 980-2 displays the similar items. If there are no similar items, then step 990-1 or 990-2 reports no match found.

In contrast to methods 601 and 602, however, the pure match, or first most likely composition of the sample displayed at step 940-1, and/or the second most likely composition of the sample displayed at step 940-2, and/or the mixture result displayed at step 970-1, and/or the mixture result displayed at step 970-2, and/or the similar items displayed at step 980-1, and/or the similar items displayed at step 980-2 are combined in the data fusion step 992 together with other external data intelligence, step 991. If the data is recognized at step 995, then the recognized data is displayed at step 996, otherwise no match found is reported at step 997.

Additionally or alternatively, an image of the sample could be captured, which could then be analyzed by an image algorithm, to determine its physical state as described above, but completely autonomously, with no input from the user(s). If the image analysis is able to determine the physical state of the sample, data analysis could be managed, so that an identification of sample that does not match the sample state would not be displayed to the end-user.

After (Post-Data Collection)

Data analysis after data collection can take place in a multitude of different routes. As described below, possible options include reanalysis of data, using combined results, to offer better identification performance, external data/sample information, analysis of the spectrum for key spectral features (functional group analysis), and analysis of previous scan identification results for chemical patterns.

Analysis & Reanalysis of Data, Using Combined Results, to Offer Better Identification Performance Data from one or more technologies can be combined to afford one result, whether that is a pure chemical, or mixture of chemicals. Two technologies can operate completely separated, as shown in FIG. 6, or the results can be combined, as shown in FIGS. 8 and 9, either after the result has been shown to a user or before. Examples of the various situations are described in Table 2.

TABLE 2

| Situation 1 | Situation 2 | Situation 3 | Situation 3 | Situation 4 |
|---|---|---|---|---|
| Technology 1 Result: chemical X Technology 2 Result: chemical X | Technology 1 Result: chemical X Technology 2 Result: chemical Y | Technology 1 Result: chemical X Technology 2 Result: chemical Y | Technology 1 Result: chemical X Technology 2 Chemical X forced into consideration during Tech 2 analysis stages | Technology 1 Result: chemical X Technology 2 Result: chemical Y Sample information provided, rules out chemical Y |
| Presented to user: Two separate result screens for Chemical X | Presented to user: Two separate result screens for Chemical X & Y | Presented to user: Resulted combined One result screen for Chemicals X & Y | Presented to user: One result screen for Chemicals X & Y | Presented to user: One result screen for Chemicals X |

External Data/Sample Information

Further to the pre-analysis stage, information about a sample could be passed into an algorithm analyzing one or more scan data spectra. A user could provide information about the physical state of the sample in the form of other external data intelligence shown in FIG. 9, such as its form (solid, liquid, or gas (e.g., in a container)), or its color. These attributes could be used to include or rule out candidates being considered by the algorithm.

Additionally or alternatively, an image of the sample could be captured, which could then be analyzed by an image algorithm, to determine its physical state as described above, but completely autonomously, with no input from the user(s). If the image analysis is able to determine the state of the sample, data analysis could be managed, so that an identification of sample that does not match the sample state would not be displayed to the end-user.

Analysis of the Spectrum for Key Spectral Features (Functional Group Analysis)

Analysis post data collection could also analyze the spectral features obtained by Raman, mid-IR (FTIR), and NIR spectroscopy. Analysis of the spectra could impart additional or secondary information. Analysis of the spectrum and corroboration of the identification results between two complementary technologies could be beneficial.

Figure 10:
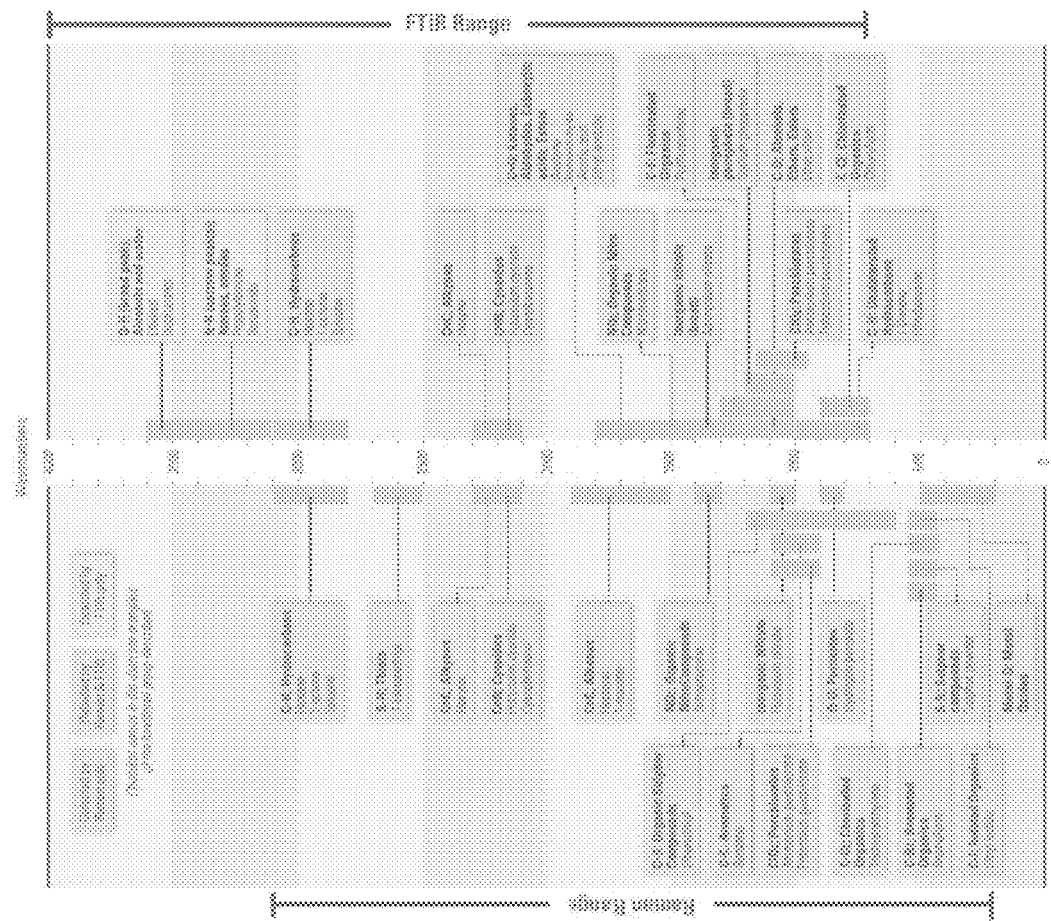
FIG. 10 is an illustration of functional groups in the Raman and FTIR wavelength ranges.

A spectrum is unique to the chemical being measured. Using this attribute, through analysis of the spectrum and analysis of the functional groups present, examples of which are shown in FIG. 10, an analysis post data collection may be able to confirm or refute the identification put forwarded by the spectrometer or offer additional sample information if the spectrometer was unable to definitively identify the chemical(s).

Analysis of Previous Scan Identification Results for Chemical Patterns.

Figure 11:
FIG. 11 is an illustration of an exemplary result screen highlighting a pattern of chemicals that could be used to manufacture other chemicals of interest.

The handheld identification device can analyze scan data information that may have been collected in the same data session (folder) using the same scan profile. The device could analyze the scan identification results within a session to look for patterns of chemicals that could be used to manufacture illicit chemicals (e.g., in an investigation of a clandestine laboratory). For instance, the device could have identified hydrogen peroxide, sulfuric acid and acetone, using either the same technology or two different technologies. As shown in FIG. 11, the device could recognize that those three chemicals are used to manufacture Triacetone triperoxide (TATP), which is a homemade explosive (HME) chemical. Such a device and capability could also be used in, but not limited to, the following environments: a chemical warfare lab, an explosive clandestine lab, or a narcotic clandestine lab. Such a device could be directed by an end-user to analyze possibilities with a selected group of chemicals or work autonomously with no end-user input.

Having thus introduced aspects of the invention, some further features and embodiments are now presented.

In one embodiment, the instrument 10 has a weight of about four pounds. It has a size of about eight inches by about four inches by about two and one half inches. The probe 20 may be used in a hand-held mode, a vial mode or mounted to another apparatus such as a robot. The probe 20 can be operated over a spectral range of 100 $cm^{-1}$ to 3000 $cm^{-1}$, such as a spectral range of 250 $cm^{-1}$ to 2850 $cm^{-1}$, at a spectral resolution in a range from about 5 $cm^{-1}$ to 11 $cm^{-1}$, such as a range from about 7 $cm^{-1}$ to 10.5 $cm^{-1}$. The power adjustable laser output can be in a range between about 50 mW to about 300 mW, such as a range between about 75 mW to about 250 mW. The anvil 22 can be operated over a spectral range of between about 650 $cm^{-1}$ to about 4,000 $cm^{-1}$, at a spectral resolution of about 4 $cm^{-1}$. Collection optics for the anvil 22 may include a solid diamond crystal ATR.

The instrument 10 may exhibit survivability that meets the requirements of MIL-STD-810G and IP67 standards. Sampling exposure may be in a manual or automatic mode. Scan delay may be user configurable with the delay up to, for example, about 120 seconds. The power supply may include removable and rechargeable batteries, such as lithium-ion batteries. An external power supply may be connected to the instrument 10, and provide about 12 V at about 1.25 A. The instrument may be operated at a temperature range of about minus 4 degrees Fahrenheit to about 122 degrees Fahrenheit on a continuous basis.

A variety of known programming and interface techniques may be used to provide for generation and/or adaptation of the response profiles 31. For example, a response profile builder may be provided. The response profile builder may be used to query a user on desired settings for a plurality of parameters 32. In some embodiments, the response profile builder is maintained on board the instrument 10, and may be further configured by the response profile manager on board a PC. In this manner, a user may quickly select and copy an existing response profile 31, and then step through a series of menus to adjust commonly used parameters 32.

It will be appreciated that any embodiment of the present invention may have features additional to those cited. Sometimes the term "at least" is used for emphasis in reference to a feature. However, it will be understood that even when "at least" is not used, additional numbers or types of the referenced feature may still be present. The order of any sequence of events in any method recited in the present application is not limited to the order recited. Instead, the events may occur in any order, including simultaneously, which is logically possible.

Various other components may be included and called upon for providing for aspects of the teachings herein. For example, additional electronic components as well as software, combinations of electronic components as well as software and/or omission thereof may be used to provide for added embodiments that are within the scope of the teachings herein.

As discussed herein, the term "software" generally refers to an instruction set provided as machine executable instructions provided as a non-transitory signal, such as stored on machine readable media. Generally, the software provides for enhanced functionality of the instrument 10. It is not a requirement however that such software reside in memory of the instrument 10. For example, software that is used on an external computer, such as a PC, to provide for configuration of the instrument 10 by use of a robust computing platform is contemplated by the teachings herein. As discussed herein, the "software" may be downloaded to the instrument, stored in the instrument, or otherwise reside in the instrument. For example, the software may be provided in read only memory (ROM) in a manner commonly referred to as "firmware."

Exemplary tools for providing at least some of the software disclosed herein include LINUXQT, from DIGIA of Finland. LinuxQT is a cross-platform application framework that is widely used for developing application software with a graphical user interface (GUI). Other comparable or desired tools may be used.

As discussed herein, the instrument is generally provided as a "handheld" instrument. This is not to imply that the instrument must fit within one's hand. That is, the instrument may have any form factor that is appropriate for field use. Accordingly, use of shared processing and other techniques to limit the size or otherwise configured the instrument are contemplated by the teachings herein. Generally, the instrument presented herein need merely be defined as adequate for supporting the sampling and analysis needs of field personnel as deemed appropriate by a user, designer, manufacturer or other similarly interested party.

When introducing elements of the present invention or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A spectrometer system, comprising:
a housing configured as a handheld device and comprising:
 a screen;
 a source of narrow band illumination configured to illuminate a sample with light;
 a sensor configured to detect Raman scattering signals in response to the narrow band illumination from the sample;
 a source of wide band illumination configured to illuminate a sample with light;
 an optical element configured to detect Fourier transform infrared signals in response to the wide band illumination from the sample;
 a memory device comprising a library of information, wherein the library of information comprises a set of Raman scattering reference spectral information and a set of Fourier transform infrared reference spectral information; and
 a processor configured to execute software instructions, wherein the software instructions are configured to:
  direct the narrow band illumination to the sample;
  detect the Raman scattering signals comprising spectral information from the sample;
  direct the wide band illumination to the sample;
  detect the Fourier transform infrared signals comprising spectral information from the sample;
  determine that the detected Raman scattering spectral information and the detected Fourier transform infrared spectral information each have a sufficient signal to noise ratio for chemical identification, wherein the noise originates from sources of measurement variability associated with the spectrometer system;
  determine a composition of the sample from a similarity between the detected Raman scattering spectral information and the set of Raman scattering reference spectral information, and from a similarity between the detected Fourier transform infrared spectral information and the set of Fourier transform infrared reference spectral information; and
  display the composition of the sample on the screen.

2. The spectrometer system of claim 1, wherein:
the software instructions are configured to combine the similarity of the Raman scattering spectral information with the similarity of the Fourier transform infrared spectral information to determine the composition of the sample.

3. The spectrometer system of claim 2, wherein:
the similarity of the Raman scattering spectral information is above a threshold value for the composition of the sample and the similarity of the Fourier transform infrared spectral information is above the threshold value for the composition of the sample.

4. The spectrometer system of claim 3, wherein:
the threshold value comprises a value of 0.05.

5. The spectrometer system of claim 1, wherein:
the software instructions are configured to determine the composition of the sample by adding a likely composition of the sample to a tag list used to determine the composition of the sample from the similarity of the Fourier transform infrared spectral information, wherein the likely composition is determined from the similarity of the Raman scattering spectral information.

6. The spectrometer system of claim 5, wherein:
the software instructions are configured to ensure consideration of the likely composition of the sample on tag list for the determination of the composition of the sample.

7. The spectrometer system of claim 1, wherein:
the software instructions are configured to determine the composition of the sample by adding a likely composition of the sample to a tag list used to determine the composition of the sample from the similarity of the Raman scattering spectral information, wherein the likely composition is determined from the similarity of the Fourier transform infrared spectral information.

8. The spectrometer system of claim 7, wherein:
the software instructions are configured to ensure consideration of the likely composition of the sample on tag list for the determination of the composition of the sample.

9. The spectrometer system of claim 1, wherein:
the source of narrow band illumination comprises a light emitting diode.
10. The spectrometer system of claim 1, wherein:
the source of narrow band illumination comprises a laser.
11. The spectrometer system of claim 1, wherein:
the source of wide band illumination comprises a electrically resistive filament.
12. The spectrometer system of claim 1, wherein:
the source of wide band illumination comprises a electrically resistive membrane.
13. The spectrometer system of claim 1, wherein:
the sensor is associated with a flexible shaft.
14. The spectrometer system of claim 1, wherein:
the optical element is associated with an anvil.
15. The spectrometer system of claim 1, wherein:
the screen comprises a touch sensitive screen.
16. The spectrometer system of claim 15, wherein:
the touch sensitive screen accepts user input about a physical state of the sample.
17. The spectrometer system of claim 16, wherein:
the software instructions are configured to use the physical state of the sample to determine the composition of the sample.
18. The spectrometer system of claim 17, wherein:
the software instructions are configured to rule out one or more candidate compositions using the physical state of the sample.
19. The spectrometer system of claim 17, wherein:
the software instructions are configured to include one or more candidate compositions using the physical state of the sample.
20. The spectrometer system of claim 1, wherein:
the software instructions are configured to analyze the composition determined from a plurality of samples to identify a potential to manufacture an illicit chemical.
21. The spectrometer system of claim 20, wherein:
the screen displays the illicit chemical.
22. The spectrometer system of claim 20, wherein:
the plurality of samples are determined during a session.

* * * * *